United States Patent [19]

Pfeiler

[11] 4,380,818
[45] Apr. 19, 1983

[54] X-RAY DIAGNOSTIC SYSTEM COMPRISING A RADIOGRAPHY UNIT WITH AN X-RAY TUBE WHICH EMITS A FAN-SHAPED RADIATION BEAM

[75] Inventor: Manfred Pfeiler, Erlangen, Fed. Rep. of Germany

[73] Assignee: Siemens Aktiengesellschaft, Berlin & Munich, Fed. Rep. of Germany

[21] Appl. No.: 267,664

[22] Filed: May 27, 1981

[30] Foreign Application Priority Data

Jun. 23, 1980 [DE] Fed. Rep. of Germany ....... 3023401

[51] Int. Cl.³ .......................... A61B 6/00; G01J 1/29; H01J 31/49; H05G 1/64
[52] U.S. Cl. .................................. 378/099; 358/111; 378/7
[58] Field of Search ................ 378/99, 7, 87; 358/111

[56] References Cited

U.S. PATENT DOCUMENTS 3,101,407  8/1963  Shipman, Jr. ......................... 378/99
3,937,965  2/1976  Vasseur ................................. 378/7
4,179,100  12/1979 Sashin et al. ........................... 378/99

Primary Examiner—Alfred E. Smith
Assistant Examiner—T. N. Grigsby
Attorney, Agent, or Firm—Hill, Van Santen, Steadman, Chiara & Simpson

[57] ABSTRACT

In an exemplary embodiment, a radiation detector for receiving the radiation emerging from the radiography subject delivers electrical output signals corresponding to the received radiation profile, generating a relative movement between the support device and the radiation beam, and with a measurand converter and a video unit for the formation of the X-ray shadow image. The radiation detector is an X-ray image intensifier with an outlet-connected television camera. A cancellation device is present which cancels the formation in the target region which is disposed immediately before the line image in the direction of movement of the line image, generated by the X-ray beam, on the target. The effect of the stray radiation on the image quality is thereby eliminated.

8 Claims, 8 Drawing Figures

X-RAY DIAGNOSTIC SYSTEM COMPRISING A RADIOGRAPHY UNIT WITH AN X-RAY TUBE WHICH EMITS A FAN-SHAPED RADIATION BEAM

BACKGROUND OF THE INVENTION

The invention relates to an X-ray diagnostic system comprising a radiographic unit with an X-ray tube, which emits a fan-shaped radiation beam, with a radiation detector for receiving the radiation emerging from the radiography subject and delivering electric output signals corresponding to the received radiation profile, with means for generating a relative movement between the support device for the radiography subject, on the one hand, and the radiation beam, disposed transversely to its longitudinal direction, on the other hand, and with a measured value converter with a display unit which, from the detector output signals, determines and displays the X-ray shadow image corresponding to the range of movement.

A diagnostic X-ray system of this type is described in the U.S. Pat. No. 3,101,407. In the case of this diagnostic X-ray system, the radiographic unit, comprised of the X-ray tube and radiation detector, is displaced in the longitudinal direction of the support device such that an X-ray shadow image can be constructed from the output signals of the radiation detector. The radiation detector is formed of an array of individual detectors. An X-ray fluoroscopy is possible only incompletely with the known diagnostic X-ray system, since a very rapid back-and-forth movement of the radiographic unit is necessary for this purpose, which is difficult to realize in practice. It is, indeed, conceivable to dispense with the detector movement during the scanning of the radiography subject if the radiation detector is designed to be long enough in the longitudinal direction of the support device so that it can detect the X-radiation emerging from the radiography subject without mechanical movement over the entire range to be scanned; however, in this case, a mechanical movement of a secondary radiation diaphragm (important for the purpose of stray radiation suppression) between the radiography subject and the radiation receiver is necessary, which leaves open a slot for the fan-shaped X-ray beam, and which is so moved with the X-ray beam that the X-ray beam, in every position, can pass through the slot and strike the radiation detector.

SUMMARY OF THE INVENTION

The object underlying the invention resides in designing a diagnostic X-ray system of the type initially cited such that, without a secondary slit diaphragm for stray radiation suppression, no negative effect of the stray radiation on the image quality occurs, even in the case of an area-type radiation detector.

In accordance with the invention, this object is achieved by virtue of the fact that the radiation detector is of the electrostatic memory type, and that a cancelling (or erasing) device is present which cancels the information in the memory area which, in the direction of movement of the line image formed by the X-ray beam, is disposed in front of the line image. In the case of the inventive diagnostic X-ray system, the charge built up e.g., on the target of a television camera, by means of stray radiation is discharged prior to the scanning of the charge for the purpose of image formation, so that the negative influence of the stray radiation on the image quality is eliminated to as great an extent as possible. In addition, in the case of utilization of an image intensifier, also the light scattering effects (background) are suppressed.

The extinguishing of the data generated on the target by the stray radiation can proceed in that the television camera, in addition to the electron gun for the image-forming scanning beam, exhibits an electron gun for a second scanning beam which leads the image-forming scanning beam on the target and extinguishes the charge potential of the target. However, it is also possible, in dispensing with a second electron gun, to provide deflection means for the image-forming scanning beam of the television camera which guide it over the area of the target to be extinguished (or blanked out), respectively, during those time intervals in which no image signal is being generated. A fluoroscopy is thus possible if the movement of the X-ray beam proceeds periodically with a speed which corresponds to the line-by-line scanning of the target of the television camera.

The invention shall be explained in greater detail in the following on the basis of the accompanying drawing sheets; and other objects, features and advantages will be apparent from this detailed disclosure and from the appended claims.

DETAILED DESCRIPTION

Figure 1:
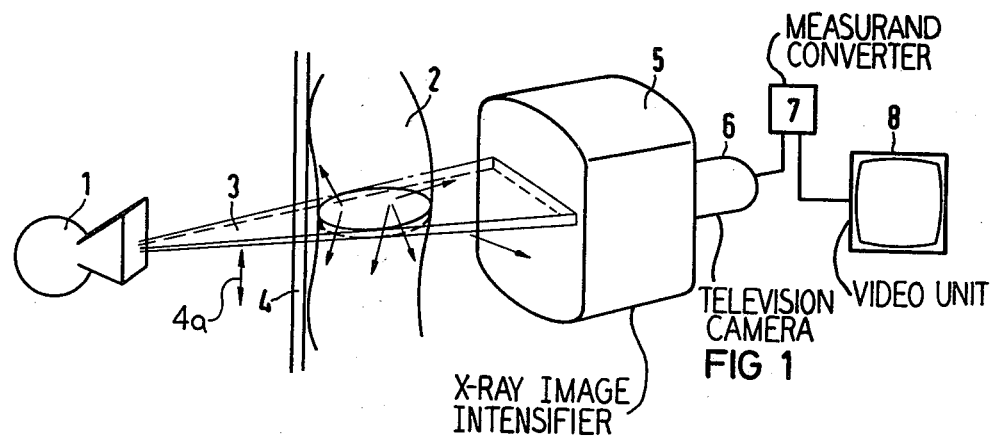
FIG. 1 illustrates the parts of a diagnostic X-ray system in accordance with the invention which are significant in terms of the invention.

In FIG. 1, an X-ray tube 1 is illustrated which irradiates a patient 2 with a fan-shaped X-ray beam 3 which runs transversely to a support device 4 for the patient 2; namely, transversely to the longitudinal direction of the support device 4. The X-radiation emerging from the patient 2 generates a line image on the inlet fluorescent screen of an X-ray fluorescent screen of an X-ray image intensifier 5, which is picked up by a television camera 6. The television camera 6 accordingly delivers electrical signals, corresponding to the line image on the inlet fluorescent screen of the X-ray image intensifier 5, to a measurand converter 7 which determines an X-ray shadow image therefrom and effects its display on a video unit 8.

For the formation of the X-ray shadow image, the X-ray beam 3 is moved a predetermined extent in the longitudinal direction (indicated by arrow 4a) of the support device 4 and thereby a predetermined region of the patient 2 is scanned. The line image on the inlet fluorescent screen of the X-ray image intensifier 5 moves correspondingly at the same time. The stray radiation, illustrated in FIG. 1, emerging from the patient 2, which strikes the inlet fluorescent screen of the X-ray image intensifier 5 outside the line image, is rendered harmless by virtue of the fact that a cancelling device is present which cancels the information which is generated by the stray radiation on the target of the television camera 7 at that location where no line image is present. The cancellation takes place immediately in front of the line image, viewed in the direction of movement of the line image on the target. For this cancellation, the television camera 6, in addition to the electron gun for the image-forming scanning beam, can have an electron gun for producing a second scanning beam which leads the image-forming scanning beam on the target and cancels the charge potential of the target. However, it is also possible to employ the image forming scanning beam itself for this cancellation, preferably in that, during those time intervals in which no image signal is being generated (e.g. during horizontal flyback), the beam from the same electron gun is guided over the area of the target which is to be cancelled.

Due to the fact that the negative effects of the stray radiation are electronically eliminated in the case of the diagnostic X-ray system illustrated in FIG. 1; i.e., only the primary radiation is utilized for the purpose of image formation, one obtains a very informative X-ray image. A fluoroscopy is possible if the movement of the X-ray beam 3 proceeds periodically with a speed which corresponds to the line-by-line scanning of the target of the television camera.

Figure 2:
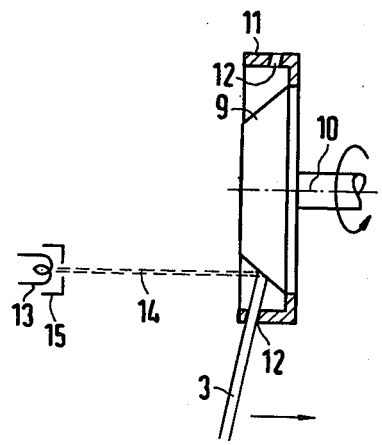
FIGS. 2 through 4 illustrate a detail of the diagnostic X-ray system according to FIG. 1.
Figure 3:
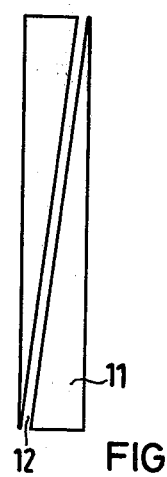
Figure 4:
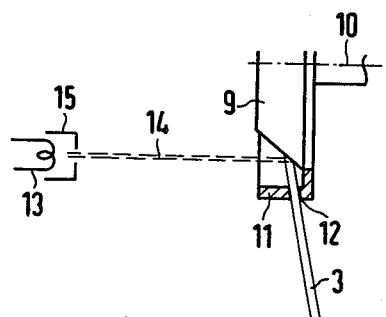

In FIGS. 2 through 4, the anode of a rotary anode X-ray tube for generating the X-ray beam 3 is referenced with 9. The anode rotates about an axis 10 and exhibits a collar 11—enclosing it as the collimator (or primary radiation diaphragm) for the formation of the fan-shaped X-ray beam 3. The collar 11 exhibits a helically extending region 12 of high X-ray transparency, whereas the diaphragm 11, for the remainder, consists of radiopaque material. In FIGS. 2 through 4, the region 12 is illustrated as a window; however, in practice, for the purpose of connection of both parts of the diaphragm 11, (which both rotate with anode 9), the diaphragm 11 except at region 12 will consist of radiopaque material. During rotation of the rotary anode 9, the X-ray beam 3 shifts in the direction of the arrow illustrated in FIG. 2. In FIG. 2, the left extreme position of the beam 3 is illustrated, whereas FIG. 4 illustrates the right extreme position. In both figures, the cathode 13, as well as the cathode plate 15, serving the purpose of formation of the electron beam 14, are illustrated. FIG. 3 illustrates the developed view of 180 degrees of the perimeter of the diaphragm 11 surrounding the anode 9.

Figure 5:
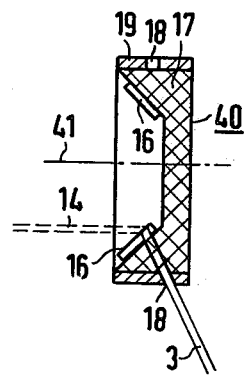
FIGS. 5 through 7 illustrate variants of the detail of FIGS. 2 through 4.

In FIG. 5, an anode 40 of an X-ray tube is illustrated which rotates about an axis 41 and which is a transmission anode, in which the X-radiation emanating from a focal spot path 16 penetrates the transparent (or radiolucent) anode member 17 and passes to the exterior from the transparent (or radiolucent) region 18 of a diaphragm 19 otherwise consisting of radiopaque material which surrounds the anode 40. The diaphragm 19 is designed with a helical region 18 corresponding to region 12 of the diaphragm 11 in FIGS. 2 through 4.

Figures 6, 7:
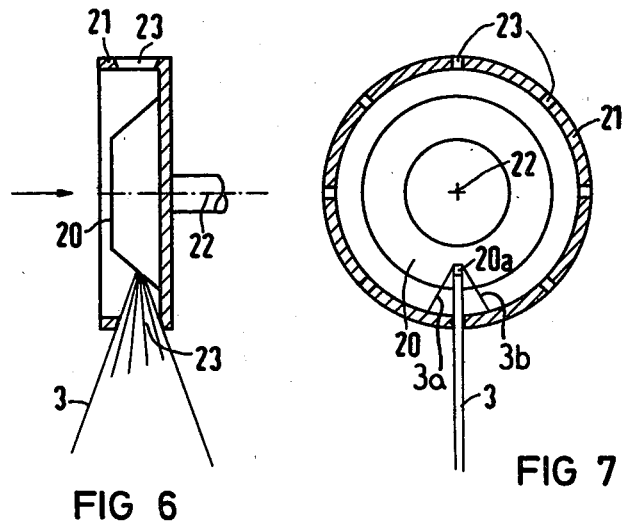

FIGS. 6 and 7 illustrate two different views of a rotary anode 20 of an X-ray tube which is surrounded by a diaphragm 21 which, like the diaphragms 11 and 19 in the FIGS. 2 through 5, surrounds the anode in a collar-like fashion. However, it possesses several line- (or stroke-) shaped slots 23 disposed parallel to the anode axis 22, whereas, for the remainder, it consists of material which is opaque to X-rays. In this embodiment, the axis 22 is disposed transversely to the longitudinal direction of the support device 4. The X-radiation emanating from the anode 20 (focal spot 20a in FIG. 7) lies in a region within which only one of the slots 23 is disposed. If a slot leaves this region, the next slot enters this region during the rotation of the anode 20 with the diaphragm 21. In this manner, a continuous scanning of a specific region of the patient 2 with a fan-shaped X-ray beam 3 is achieved.

For the diaphragms illustrated in FIGS. 2 through 7, it is a fact that, due to the fixed connection with the X-ray tube anode, they rotate with the latter, and that it is therefore possible, with the aid of a synchronization device for synchronizing the rotation of the rotary anode with the scanning of the target of the television camera 6, to obtain a movement of the line image on the inlet fluoroescent screen of the X-ray image intensifier 5 which proceeds synchronously with this scanning, so that a fluoroscopy is possible.

The invention is described in conjunction with a television camera comprising an electrostatic-storing target. However, also other radiation detectors of the electrostatic memory type, such as semiconductor plates, are applicable. In addition, the image intensifier can be dispensed with if an X-ray sensitive television camera is employed.

Figure 8:
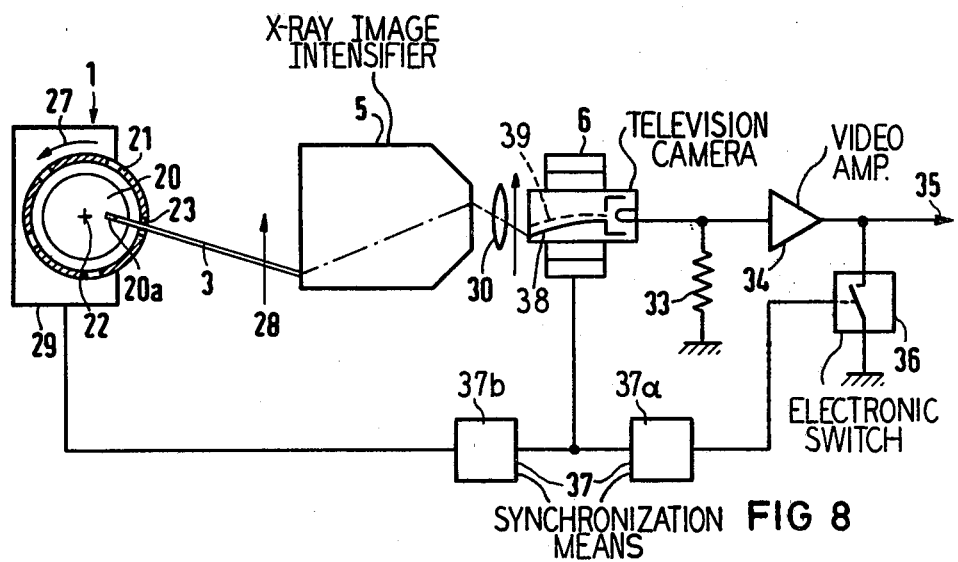
FIG. 8 illustrates a circuit arrangement for the diagnostic X-ray system according to FIG. 1.

In the X-ray diagnostic system illustrated in FIG. 8, the focus 20a of the X-ray tube 1 is illustrated, from which focus an X-ray beam emanates which, by means of a hollow-cylindrical diaphragm 21 rotating about the axis 22, is defined in a fan-shaped fashion through the successive axial slots 23. During the rotation of the diaphragm 21 in the direction of the arrow 27, the fan-shaped X-ray beam 3 travels in the direction of the arrow 28 and thus scans the inlet fluorescent screen of the X-ray image intensifier 5. The X-ray tube 1 is arranged with the diaphragm 21 in a housing 29.

Between the X-ray intensifier 5 and the television camera 6 a lens (or optical) system 30 is disposed. The television camera 6 possesses a target for charge storage, corresponding to the respectively picked-up image, which is scanned by an electron beam. The electron beam scans the actual image which is generated by the X-ray beam 3, on the one hand, whereas, in time intervals in which no image scanning takes place, it cancels the charge on the target, because then the video signal, generated via a video amplifier 34, does not reach the output 35, but is diverted by means of an electronic switch 36. The switch 36, as well as the rotation of the diaphragm 21 and the deflection of the electron beam of the television camera 6, are synchronized by synchronization means 37. The output signal of the television camera 6, generated by the electron beam, which is either the video signal or a signal which is dependent upon the stray radiation and therefore must be diverted by the switch 36, is tapped at a load resistance 33. Thus, in the example according to FIG. 8, during those time intervals in which no picture (or video) signal is generated; e.g., during horizontal fly-back (or retrace), the electron beam of the television camera 6 which scans the target is guided, with the aid of the synchronization means 37, over the region of the target which is to be canceled, and the output signal thus generated at the load resistance 33 is diverted by the electronic switch 36 so that it does not contribute to the formation of the image.

It will be apparent that many modifications and variations may be effected without departing from the scope of the novel concepts and teachings of the present invention.

SUPPLEMENTAL DISCUSSION

FIG. 8 may be taken as illustrating an embodiment where a single electron gun continuously produces an electron beam (without blanking out of the beam during horizontal retrace intervals). Thus, after a vertical retrace operation during which the switch 36 is closed, the beam such as indicated at 38 in FIG. 8 may execute a first horizontal retrace deflection immediately in advance of scanning of a first horizontal line by means of the beam 3. Then, with the registration of the scanning beam 3 with the first line on the camera target, the beam scans at the normal deflection rate such first line on the target (which line has already been neutralized as to stray light in the preceding horizontal retrace interval). During the next horizontal retrace interval, the beam is stepped to register with the second horizontal line of the target as diagrammatically indicated by the dash line at 39 in FIG. 8. Thus, any stray charge on the second line of the target is neutralized immediately in advance of the image-forming deflection operation.

It will be apparent that an encoder device may rotate with the shaft of anode 20 and be disposed in relation to the slots 23, so that the encoder triggers a retrace deflection of the electron beam along the first horizontal line of the camera target just before the collar 21 reaches the position for scanning the first line (which position may be that illustrated in FIG. 8). At the completion of the retrace deflection of the electron beam 38, a further pulse from the encoder rotating with collar 21 and anode 20 may cause the synchronizing means 37a to place switch 36 in the open position as shown in FIG. 8. At the completion of the first image-forming scan of the electron beam, a further pulse from the encoder will activate the vertical deflection of the camera tube to shift the electron beam to the position such as indicated at 39 for scanning the second line on the camera target, switch 36 then being closed and the retrace deflection initiated. It will thus be apparent that the encoder rotating with anode 20 can generate a number of pulses equal to twice the number of horizontal lines to be scanned, for each arc of rotation corresponding to the separation between successive slots 23 of collar 21. By way of example, the vertical deflection of the electron beam of the camera tube may be under the control of a counter which drives a digital to analog converter in such a way that a step type deflection waveform is generated, synchronized with the rotation of the anode 20, so that the electron beam is stepped in the vertical direction at the end of each image-forming horizontal deflection. For the example of an encoder rotating with anode 20, component 37a may be a bistable circuit which responds to a pulse at the beginning of each horizontal retrace to close switch 36, and responds to the next encoder pulse at the beginning of an image-forming deflection to open switch 36, and so on alternately. With the provisions of triggering of each image-forming horizontal deflection and of each horizontal retrace deflection, the speed of movement of the beam in each horizontal direction may be equal, for example. The generation of such a triangular type of deflection waveform is clearly within the skill of the art. It is directly analogous to the problem of horizontal deflection in conventional television technology, but with alternate pulses producing a ramp type waveform of opposite polarity but of the same slope.

Reference numerals 3a, 3b in FIG. 7 indicate the conical configuration of the beam 3 emanating from the focal spot 20a, such that the beam configuration of FIG. 6 is swept in the direction of arrow 28, FIG. 8, by arcuate movement of the slot 23 (while the angular location of the spot 20a progresses along the surface of anode 20 so as to remain at the same angular orientation to axis 22 as shown in FIG. 7, continuously during the continuous rotation of anode 20 and collar 21).

The control of two alternately scanning electron beams is also represented in FIG. 8, where the beam path 39 would be produced by the cancelling electron gun and would sweep a given line on the target of the camera just prior to the sweep of the image-forming scanning beam as indicated at 38. In this case, each electron gun would receive a horizontal blanking signal while the other electron gun was active, the beam 39 being blanked during its retrace interval while the image-forming scanning beam 38 is executing an image-forming horizontal scan, the beam 39 being unblanked, and switch 36 being closed during a subsequent cancelling scan operation by the beam 39 (with the returning beam 38 blanked in the conventional manner). In this case, each beam could be unblanked in one direction of horizontal scanning and blanked out during a return horizontal scan. The adjustment could be such as to permit a slower movement of the beam 39 than would be necessary if the beam 39 were to complete a cancelling horizontal trace within the conventional retrace time of the beam 38.

I claim as my invention:

1. A diagnostic radiology system comprising a radiographic unit having a support for a radiography subject, having an X-ray tube, which emits a fan-shaped radiation beam, having a radiation detector for receiving the radiation emerging from the radiography subject, which radiation detector delivers electric output signals corresponding to the received radiation profile, having means for generating relative movement between the support for the radiography subject and the radiation beam over an excursion range, and having a measurand converter which, from the detector output signals, determines the X-ray shadow image corresponding to the excursion range and provides an output for effecting display of such image, characterized in that the radiation detector (5, 6) is of the electrostatic memory type for electrostatically storing signals in accordance with the received radiation, and that a canceling device is present which cancels the stored signals in the memory area which, in the direction of movement of the line image formed by the X-ray beam (3), are disposed before the line image.

2. A diagnostic radiology system according to claim 1, characterized in that the radiation detector comprises an X-ray image intensifier (5), and a television camera (6) coupled with the output of the image intensifier.

3. A diagnostic radiology system according to claim 2, characterized in that the television camera (6) comprises a target for electrostatically storing charge signals in accordance with received radiation, an electron gun for producing an image-forming scanning beam for scanning the target to supply the detector output signals, and an electron gun for producing a second scanning beam which leads the image-forming scanning beam on the target and which cancels the charge signals stored by the target.

4. A diagnostic radiology system according to claim 2, with the television camera (6) having a target for storing signals in accordance with received radiation characterized in that deflection means for the image-forming scanning beam of the television camera (6) are present which guide it over the region of the target which is to be canceled during those time intervals in which no image signal is being generated.

5. A diagnostic radiology system according to claim 1, characterized in that the movement of the X-ray beam (3) proceeds periodically with a speed which corresponds to the line-by-line scanning of the memory area of the radiation detector (5, 6).

6. A diagnostic radiology system according to claim 5, characterized in that a rotary anode X-ray tube comprising a diaphragm (11, 19, 21), rotating with the rotary anode (9, 20, 40), for the X-ray beam (3), and a synchronization device (37) for synchronization of the rotation of the rotary anode (9, 20, 40) with the scanning of the memory area are present.

7. A diagnostic radiology system according to claim 6, characterized in that the diaphragm (11, 19) comprising a collar of radiopaque material surrounding the rotary anode (9, 40), having a helically extending region (12, 18) of high X-ray transparency.

8. A diagnostic radiology system according to claim 6, characterized in that the diaphragm (21) comprises a collar of radiopaque material, surrounding the rotary anode (20), and including a plurality of line shaped regions (23) of high X-ray transparency which are disposed parallel to the anode axis (22).

* * * * *